United States Patent
Kim et al.

(10) Patent No.: US 11,406,733 B2
(45) Date of Patent: Aug. 9, 2022

(54) POROUS MICROPARTICLES OF BIODEGRADABLE POLYMER, AND POLYMER FILLER COMPRISING SAME

(71) Applicant: SAMYANG HOLDINGS CORPORATION, Seoul (KR)

(72) Inventors: Jin Su Kim, Incheon (KR); Wang Soo Shin, Daejeon (KR); Na Jeong Park, Suwon-si (KR); Young Joo Koh, Daejeon (KR); Jun Bae Kim, Daejeon (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 174 days.

(21) Appl. No.: 16/468,828

(22) PCT Filed: Aug. 10, 2017

(86) PCT No.: PCT/KR2017/008704
§ 371 (c)(1),
(2) Date: Jun. 12, 2019

(87) PCT Pub. No.: WO2018/110792
PCT Pub. Date: Jun. 21, 2018

(65) Prior Publication Data
US 2020/0069839 A1    Mar. 5, 2020

(30) Foreign Application Priority Data

Dec. 13, 2016 (KR) .................. 10-2016-0169309
Aug. 7, 2017 (KR) .................. 10-2017-0099514

(51) Int. Cl.
*A61K 9/16* (2006.01)
*A61L 27/26* (2006.01)
*A61L 27/56* (2006.01)
*C08J 9/26* (2006.01)

(52) U.S. Cl.
CPC .............. *A61L 27/26* (2013.01); *A61L 27/56* (2013.01); *C08J 9/26* (2013.01); *C08J 2367/04* (2013.01)

(58) Field of Classification Search
CPC .......... A61K 9/14; A61K 9/141; A61K 9/143; A61K 9/145; A61K 9/16; A61K 9/1605; A61K 9/1611; A61K 9/1617; A61K 9/50; A61K 9/5036; A61K 9/5047
See application file for complete search history.

(56) References Cited

U.S. PATENT DOCUMENTS

| | | | |
|---|---|---|---|
| 2002/0090398 A1* | 7/2002 | Dunn ................... | A61K 9/0024 424/486 |
| 2005/0142201 A1* | 6/2005 | Rashba-Step ............ | B01J 13/06 424/489 |
| 2009/0317478 A1 | 12/2009 | Han et al. | |
| 2010/0215702 A1 | 8/2010 | Supèr et al. | |
| 2016/0222193 A1 | 8/2016 | Bringley et al. | |

FOREIGN PATENT DOCUMENTS

| | | | | |
|---|---|---|---|---|
| EP | 3017841 A | 5/2016 | | |
| JP | 2009-144012 A | 7/2009 | | |
| JP | 2016-87474 A | 5/2016 | | |
| KR | 10-0840394 B1 | 6/2008 | | |
| KR | 10-2010-0065309 A | 6/2010 | | |
| KR | 10-2011-0031378 A | 3/2011 | | |
| KR | 10-2011-0075618 A | 7/2011 | | |
| KR | 10-1142234 B1 | 7/2012 | | |
| KR | 10-1517256 B1 | 5/2015 | | |
| KR | 10-2015-0108956 A | 10/2015 | | |
| WO | WO-2009014441 A2 * | 1/2009 | ............ | A61K 31/05 |
| WO | WO 2010/004287 A2 | 1/2010 | | |

OTHER PUBLICATIONS

Indian Office Action and Search Report, dated Jul. 17, 2020, for Indian Application No. 201947027416, with an English translation.
International Search Report (PCT/ISA/210) issued in PCT/KR2017/008704, dated Nov. 22, 2017.

* cited by examiner

*Primary Examiner* — Micah Paul Young
(74) *Attorney, Agent, or Firm* — Birch, Stewart, Kolasch & Birch, LLP

(57) ABSTRACT

The present invention relates to porous microparticles of a biodegradable polymer, and a polymer filler comprising the same.

7 Claims, 5 Drawing Sheets

<Example 1>

<Comparative Example 1>

POROUS MICROPARTICLES OF BIODEGRADABLE POLYMER, AND POLYMER FILLER COMPRISING SAME

TECHNICAL FIELD

The present invention relates to porous microparticles of biodegradable polymer, and polymeric filler comprising the same.

BACKGROUND ART

Many people wanted healthy life in the past, but as the era of aging population comes, people want beautiful life as well as healthy life. As people wanting beautiful life increases, related various products are appearing on the market.

Products for preventing and treating the aging have been on the market in various fields such as food, drugs, cosmetics, etc. Among them, botulinum toxin and facial fillers are the representative products in the field of drugs. Botulinum toxin was used at first for the purpose of muscle relaxation, but it is now used overwhelmingly for aesthetic purpose, as a form for facial wrinkle improvement. In addition, the market for fillers such as collagen, hyaluronic acid, etc., which are safe and bioabsorbable and thus can be used as an agent for filling skin volume, is growing rapidly.

Filler products are classified into four (4) generations according to the course of development.

The 1$^{st}$ generation filler used collagen ingredient extracted from animals. However, it caused allergic reaction to collagen, and the retention time was as short as 1 to 3 months. Accordingly, this filler is nearly not used at present.

The 2$^{nd}$ generation filler is a filler of hyaluronic acid ingredient, and it takes now 90% share of the market. Hyaluronic acid is a safe ingredient present in joint fluid, cartilage, skin, etc. of human body. However, non-crosslinked hyaluronic acid is decomposed only within one day after hypodermic injection, resulting in no effect. Thus, many manufacturers are crosslinking hyaluronic acid to produce fillers showing the effect for 1 to 1.5 years. At this time, as the amount of crosslinking agent used for the crosslinking increases, toxicity can be caused to the human body, and thus the technology to remove the used crosslinking agent perfectly is important.

The 3$^{rd}$ generation filler includes calcium filler made out of a material which is not decomposed easily in living body, and polymethylmethacrylate (PMMA) filler which is undecomposable permanently. In case of calcium filler, since it is not decomposed easily, if the procedure is done well, there is an advantage of maintaining the effect for a long time. However, if the result after the procedure is unsatisfactory, there is a disadvantage of waiting for a long time until the injected material is bio-decomposed completely. In case of PMMA filler, the permanent effect may be expected, but if the procedure goes wrong, there is a disadvantage of difficult removal. In addition, since it remains for a long time in human body and the probability of causing side effect is high, it is at risk of being kicked out from the market.

The 4$^{th}$ generation filler is a filler using biodegradable polymer, and it is now in the spotlight of the market. Differently from hyaluronic acid filler which retains the skin volume by the volume of the product itself, biodegradable polymer filler induces generation of collagen as the polymer is decomposed, and thus naturally recovers and retains the volume. The retention time can be controlled by the molecular weight of the polymer, and the currently marketed products can retain the volume for various periods of time in 1 to 4 years. However, there is a disadvantage that the initial volume decreases sharply within 1 week after the procedure, and then the volume comes up slowly over a period of from 4 weeks to 6 months.

Korean Patent No. 1517256 discloses a process for preparing polycaprolactone-comprising microparticles wherein the process comprises the steps of: solubilizing a polycaprolactone polymer and subsequently mixing the solubilized polycaprolactone polymer with a liquid comprising a surfactant and having a viscosity ranged between 20 and about 10,000 cP; and forming polycaprolactone-comprising microparticles from the obtained solution; and microparticles obtained by the process, having at least the characteristics of: i) a diameter ranged between 5 and 100 µm ii) homogenous density, form and content, iii) essentially spherical microspheres, and iv) smooth surface. However, such microparticles have soft and smooth surface, and the filler prepared by using the same has a disadvantage that the initial volume decreases sharply within 1 week after the procedure, and then the volume comes up slowly over a period of from 4 weeks to 6 months.

Korean Patent No. 1142234 discloses an injectable agent comprising porous biodegradable polymer microparticles and an aqueous solution of a temperature-sensitive, phase-transitionable, biocompatible polymer, wherein the agent is converted to a gel phase in vitro and injected into the body, and after the injection into the body, it is used as a bulking agent or filler for treating urinary incontinence. The biodegradable polymer microparticles have a porosity ratio of 80 to 96%, a pore diameter of 25 to 500 µm, and a particle diameter of 100 to 5,000 µm, and as such, the particle size is so large that injection thereof is very difficult and use thereof for facial application is nearly impossible.

Therefore, there is a continuing need for polymer filler which is of a biodegradable polymer material that is biocompatible and induces collagen generation, and can control the retention time long and variously, while the filler can retain the volume immediately after the procedure like the existing hyaluronic acid filler, and has a small particle size so as to be injectable with a thin injection needle, resulting in minimizing the pain and foreign body sensation felt by the patient after the injection.

Problems to be Solved

The present invention is intended to resolve the above-stated problems of the conventional filler products, and has an object of providing a polymer filler which is of a biodegradable polymer material that induces collagen generation after the injection into human body and has a long retention time, and at the same time, that can retain the volume immediately after the procedure like the existing hyaluronic acid filler and has a small particle size so as to be injectable with a thin injection needle, resulting in minimizing the pain and foreign body sensation felt by the patient after the injection.

Technical Means

One aspect of the present invention provides porous microparticle of biodegradable polymer, having
i) spherical shape,
ii) particle diameter of 10 to 200 µm,
iii) pore with a diameter of 0.1 to 20 µm, and
iv) porosity ratio of 5 to 50%.

Another aspect of the present invention provides polymer filler comprising the porous microparticle of biodegradable polymer; and one or more biocompatible carriers.

Effect of the Invention

Due to the porous polymer particle, the polymer filler according to the present invention can have a larger volume than the existing products based on the same mass, and thus by the volume of polymer, it can provide the effect of retaining the volume even immediately after the procedure.

The polymer filler according to the present invention is used with mixing the polymer microparticle and a carrier similarly to the existing polymer fillers, and the carrier is absorbed first like the conventional products, but the remaining polymer is biodegraded slowly while inducing self-collagen generation of peripheral tissues over a long period of time, thereby exhibiting a longer retention time than hyaluronic acid fillers. In addition, despite the first absorption of the carrier, the porous particle polymer filler according to the present invention has nearly no effect of volume reduction since the volume of polymer itself is larger than the existing polymer fillers. Furthermore, by controlling the porosity ratio of the porous particle and thereby adjusting the degree of volume reduction immediately after the procedure, the volume can be provided at a desired level.

Therefore, according to the particle size and the porosity ratio, the biodegradable polymer filler according to the present invention can be used as filler for human in various parts of human body including face. Furthermore, it has a small particle size so as to be injectable with a thin injection needle, and thus it can minimize the pain and foreign body sensation felt by the patient after the injection.

DETAILED DESCRIPTION

Figure 1:
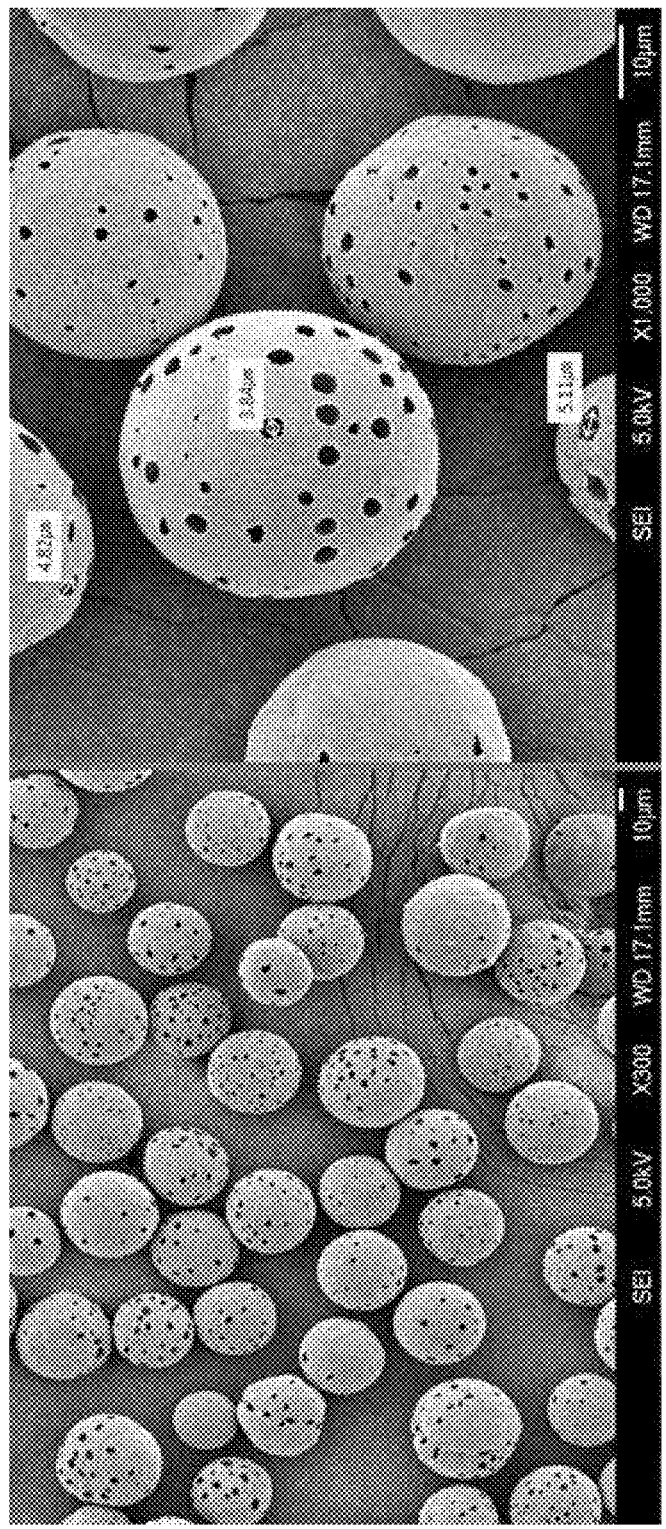
FIG. 1 shows scanning electron microscope (SEM) photographs of an embodiment of the porous microparticle of biodegradable polymer used in the biodegradable polymer filler according to the present invention.

The present invention is explained in more detail below.

The polymer filler of the present invention uses porous microparticle of biodegradable polymer, prepared from a polymer having biocompatibility and biodegradability. In the present invention, the biodegradable polymer, which can be used for preparing the porous microparticle of biodegradable polymer, can be at least one selected from the group consisting of poly(lactic acid), poly(glycolic acid), poly (dioxanone), poly(caprolactone), poly(lactic acid-co-glycolic acid), poly(dioxanone-co-caprolactone), poly(lactic acid-co-caprolactone), derivatives thereof and copolymers thereof. Preferably, the biodegradable polymer is poly(lactic acid) or poly(caprolactone), and more preferably poly (caprolactone).

Also, in order to maintain the filler retention period for 2 years or longer, the biodegradable polymer can have a number average molecular weight (Mn) in a range of preferably 10,000 to 1,000,000 g/mol, and more preferably 10,000 to 100,000 g/mol.

The particle size of the porous microparticle of biodegradable polymer should be smaller than the diameter of the injection needle so that it can be injected, and the shape of the particle is substantially in spherical form so as not to cause pain to the patient and not to be felt by touch.

In an embodiment, the particle size (particle diameter) of the porous microparticle of biodegradable polymer can be typically 200 μm or less, and it preferably has a diameter of 10 μm or greater in order not to be eaten by macrophage in living tissues. In a preferable embodiment, the porous microparticle of biodegradable polymer has a diameter of 10 to less than 100 μm, more preferably 10 to 80 μm, still more preferably 10 to 50 μm, and most preferably 20 to 40 μm.

In a preferable embodiment, as the standard of particle size distribution, the porous microparticle of biodegradable polymer has $d_{10}$ of greater than 20 μm and $d_{90}$ of less than 100 μm, preferably $d_{10}$ of greater than 20 μm and $d_{90}$ of less than 60 μm, and more preferably $d_{10}$ of greater than 25 μm and $d_{90}$ of less than 40 μm.

Also, in a preferable embodiment, the porous microparticle of biodegradable polymer should have a span value, which shows uniform distribution of particles, of less than 1, preferably less than 0.8, and more preferably less than 0.6. The span value becomes greater as the particle size distribution becomes broad, and it becomes close to 0 as the particle size distribution becomes narrow. The span value is calculated by the following equation:

$$span = \frac{D_{90} - D_{10}}{D_{50}}$$

[Definitions of $D_{10}$, $D_{50}$ and $D_{90}$: Size values corresponding to 10%, 50% and 90%, respectively, of the maximum value in accumulated distribution of particles, represented as the particle sizes corresponding to $\frac{1}{10}$, $\frac{5}{10}$ and $\frac{9}{10}$, respectively, of the particle size distribution curve showing the relatively accumulated amounts of particles according to the size) when it is measured, plotted and divided into 10 fractions.]

Since the porous microparticle of biodegradable polymer used in the present invention has pores, it has a larger volume per the same mass according to the porosity ratio.

In an embodiment, the porosity ratio of the porous microparticle of biodegradable polymer can be 5 to 50%, preferably 10 to 50%, and more preferably 10 to 30%.

In the present invention, the "porosity ratio" is obtained according to the following equation:

Porosity ratio=(Volume of porous polymer microparticle−Volume of non-porous polymer microparticle)/Volume of porous polymer microparticle× 100

The pore size (diameter) of the porous microparticle of biodegradable polymer according to the present invention can be 0.1 μm to 20 μm, and preferably 0.1 to 10 μm.

As a method for preparing such porous microparticle of biodegradable polymer, an emulsification method, a solvent evaporation method, a precipitation method or other generally used in this field of art can be used, and the present invention is not limited by any method for preparing porous microparticle.

The amount of the porous microparticle of biodegradable polymer contained in the polymer filler of the present invention can be typically 10 to 50% by weight, and more concretely 10 to 30% by weight, based on 100% by weight of the polymer filler, and it can be adjusted according to the desired volume effect of the desired injection part.

The polymer filler of the present invention also comprises one or more biocompatible carriers. Such a carrier is absorbed in body typically within 1 day to 6 months after the injection.

In an embodiment, a carrier selected from carboxymethyl cellulose, hyaluronic acid, dextran, collagen and combinations thereof can be used as the biocompatible carrier.

The amount of the biocompatible carrier contained in the polymer filler of the present invention can be typically 50 to 90% by weight, and more concretely 70 to 90% by weight, based on 100% by weight of the polymer filler.

As well as the ingredients explained above, additive ingredients—for example, a lubricant such as glycerin, phosphate buffer or the like conventionally comprised in an injection formulation—can be further comprised in the biocompatible carrier.

The polymer filler of the present invention can be an injection formulation preferably. An injection formulation of the polymer filler of the present invention can be provided as being contained in a sterilized injection syringe or a sterilized vial, and it has high use convenience since no pretreatment is needed, it is safe since 100% thereof is biodegraded over a predetermined time after the injection leaving no foreign substance in living tissues, and it does not cause allergic reaction since it contains no substances derived from animal at all.

In addition, as compared with the existing polymer product (for example, polymer content of 30%), the polymer filler of the present invention can provide a greater volume effect with the same amount of polymer, and thus the volume effect can be maintained even if the carrier is absorbed. Therefore, the polymer filler of the present invention can be used preferably for wrinkle improvement, facial plastic procedure or body plastic procedure.

The present invention is explained in more detail by the following examples. However, the following examples are intended only to illustrate the present invention, and should not be interpreted as limiting the scope of the present invention in any manner.

EXAMPLE

Example 1

By using polycarprolactone (PCL) with a number average molecular weight of 50,000 g/mol, porous microparticles of biodegradable polymer (porosity ratio: 10%) in 20 to 40 μm diameter were prepared through a membrane emulsification method. That is, 1 g of the biodegradable polymer PCL and 0.2 g of tetradecane for pore formation were dissolved in 20 g of methylene chloride, and homogeneously mixed in a PVA aqueous solution to prepare porous microparticles of biodegradable polymer with porosity ratio of 10%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 30% by weight of the porous microparticles and 70% by weight of the carrier.

Example 2

By using polycarprolactone (PCL) with a number average molecular weight of 50,000 g/mol, porous microparticles of biodegradable polymer (porosity ratio: 20%) in 20 to 40 pan diameter were prepared through a membrane emulsification method. That is, 1 g of the biodegradable polymer PCL and 0.3 g of tetradecane for pore formation were dissolved in 20 g of methylene chloride, and homogeneously mixed in a PVA aqueous solution to prepare porous microparticles of biodegradable polymer with porosity ratio of 20%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 30% by weight of the porous microparticles and 70% by weight of the carrier.

Example 3

By using polycarprolactone (PCL) with a number average molecular weight of 50,000 g/mol, porous microparticles of biodegradable polymer (porosity ratio: 10%) in 20 to 40 μm diameter were prepared through a membrane emulsification method. That is, 1 g of the biodegradable polymer PCL and 0.2 g of tetradecane for pore formation were dissolved in 20 g of methylene chloride, and homogeneously mixed in a PVA aqueous solution to prepare porous microparticles of biodegradable polymer with porosity ratio of 10%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 40% by weight of the porous microparticles and 60% by weight of the carrier.

Example 4

By using polycarprolactone (PCL) with a number average molecular weight of 50,000 g/mol, porous microparticles of biodegradable polymer (porosity ratio: 20%) in 20 to 40 μm diameter were prepared through a membrane emulsification method. That is, 1 g of the biodegradable polymer PCL and 0.3 g of tetradecane for pore formation were dissolved in 20 g of methylene chloride, and homogeneously mixed in a PVA aqueous solution to prepare porous microparticles of biodegradable polymer with porosity ratio of 20%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was based on 100% by weight of the mixture, 40% by weight of the porous microparticles and 60% by weight of the carrier.

Example 5

By using polycarprolactone (PCL) with a number average molecular weight of 50,000 g/mol, porous microparticles of biodegradable polymer (porosity ratio: 10%) in 20 to 40 μm diameter were prepared through a microfluidic method. That is, 1 g of the biodegradable polymer PCL and 0.2 g of tetradecane for pore formation were dissolved in 20 g of methylene chloride, and uniformly fed into a PVA aqueous solution by using a microfluidic device to prepare porous microparticles of biodegradable polymer with porosity ratio of 10%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 30% by weight of the porous microparticles and 70% by weight of the carrier.

Example 6

By using polycarprolactone (PCL) with a number average molecular weight of 50,000 g/mol, porous microparticles of biodegradable polymer (porosity ratio: 20%) in 20 to 40 μm diameter were prepared through a microfluidic method. That is, 1 g of the biodegradable polymer PCL and 0.3 g of tetradecane for pore formation were dissolved in 20 g of methylene chloride, and uniformly fed into a PVA aqueous solution by using a microfluidic device to prepare porous microparticles of biodegradable polymer with porosity ratio of 20%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 30% by weight of the porous microparticles and 70% by weight of the carrier.

Example 7

By using polylactic acid (PLA) with a number average molecular weight of 80,000 g/mol, porous microparticles of biodegradable polymer (porosity ratio: 10%) in 20 to 40 μm diameter were prepared through a membrane emulsification method. That is, 1 g of the biodegradable polymer PLA and 0.2 g of tetradecane for pore formation were dissolved in 20 g of methylene chloride, and homogeneously mixed in a PVA aqueous solution to prepare porous microparticles of biodegradable polymer with porosity ratio of 10%.

The prepared porous microparticles of biodegradable polymer was mixed with a carrier prepared from 3% by weight of carboxymethyl cellulose, 27% by weight of glycerin and 70% by weight of phosphate buffer. At that time, the mixing ratio was, based on 100% by weight of the mixture, 30% by weight of the porous microparticles and 70% by weight of the carrier.

Comparative Example 1

Commercially available facial filler (Ellanse®) using PCL as the raw material was purchased.

Comparative Example 2

Commercially available facial filler (Sculptra®) using polylactic acid (PLA) as the raw material was purchased.

Experimental Example 1

Figure 2:
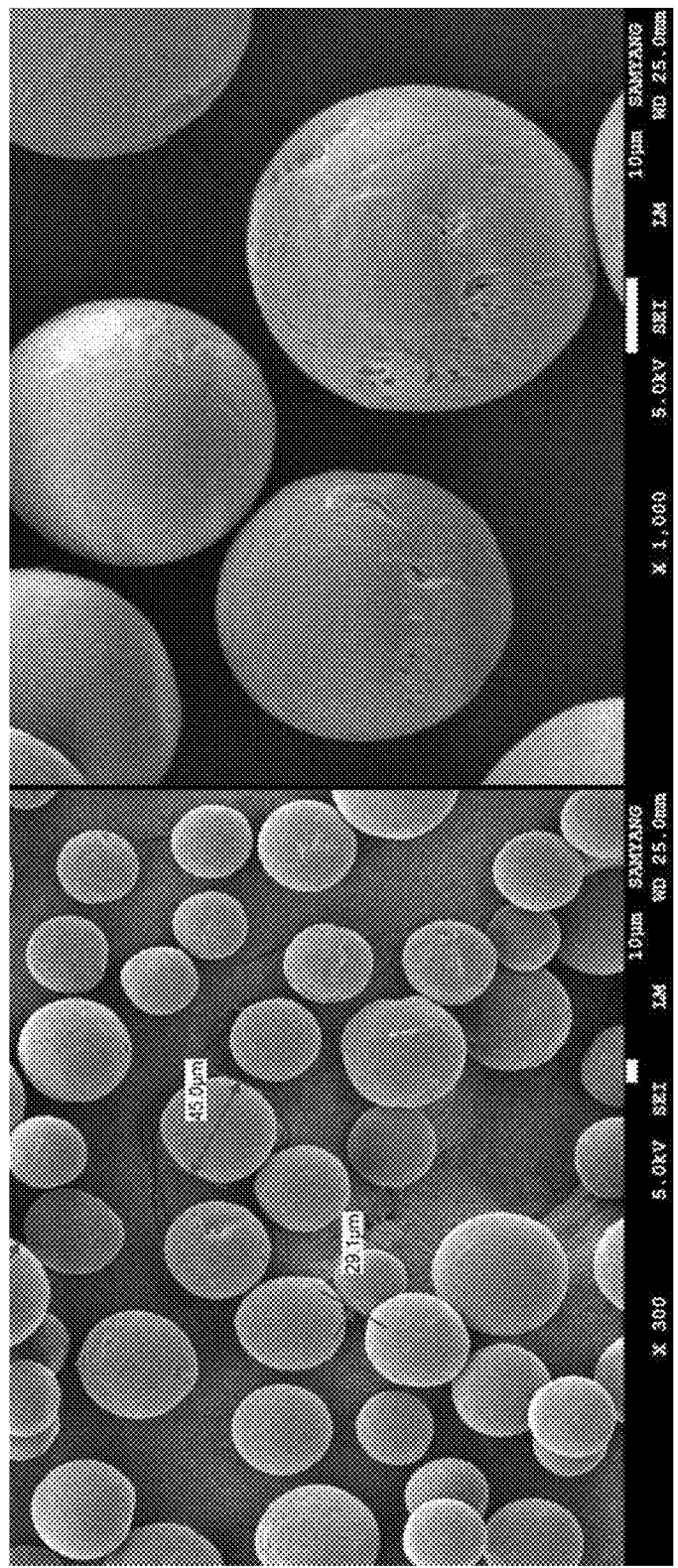
FIG. 2 shows scanning electron microscope (SEM) photographs of the microparticle according to Comparative Example 1 of the present invention.
Figure 3:
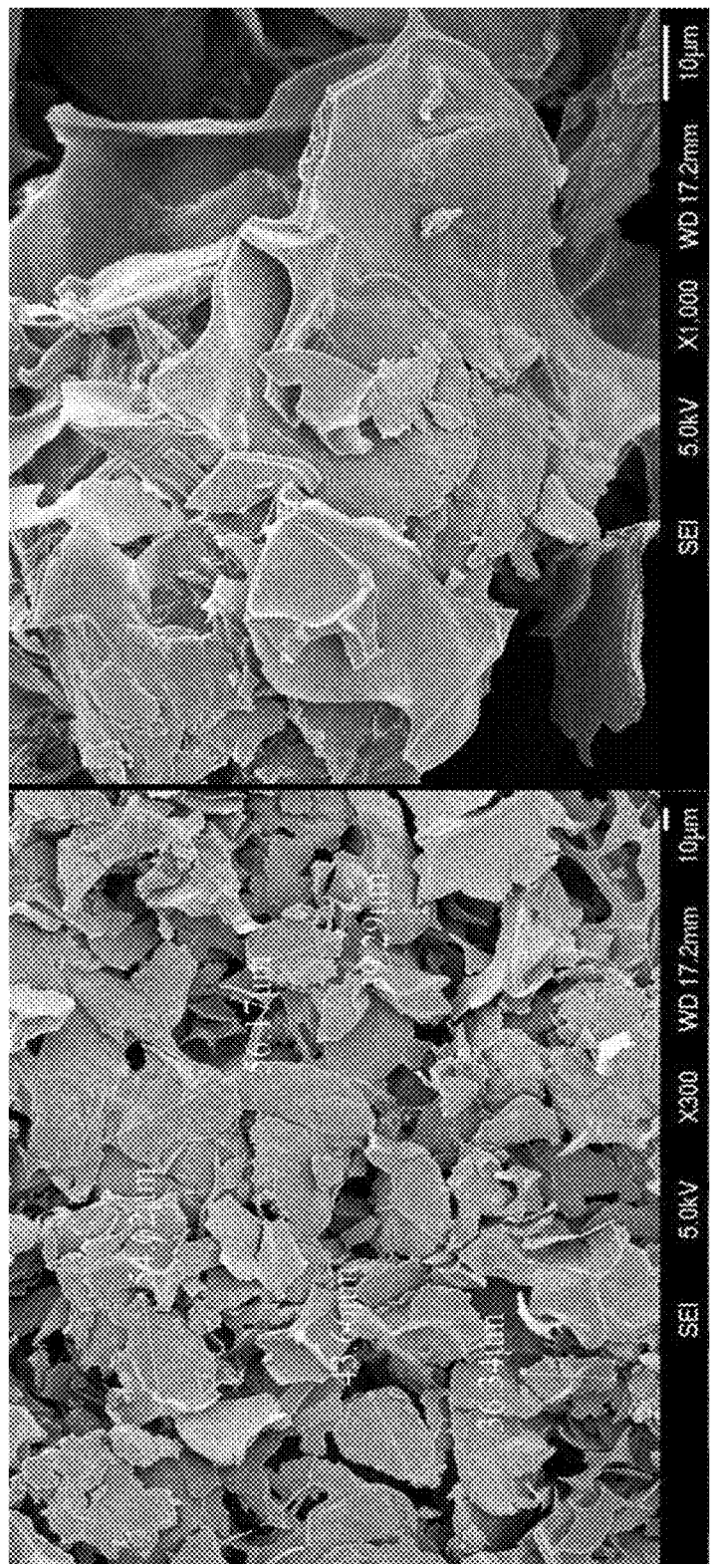
FIG. 3 shows scanning electron microscope (SEM) photographs of the microparticle according to Comparative Example 2 of the present invention.

The porous microparticles of biodegradable polymer obtained in the above Example 1 and the microparticles of Comparative Examples 1 and 2 were observed with scanning electron microscope (SEM). The results are shown in FIG. 1, FIG. 2 and FIG. 3, respectively. As shown in FIG. 1, the porous microparticles of biodegradable polymer according to the present invention had particle diameter of 20 to 40 μm and pore diameter of 0.1 to 6 μm, that is, smaller particle size and uniform pores with smaller diameter as compared with the existing products.

Experimental Example 2

Figure 4:
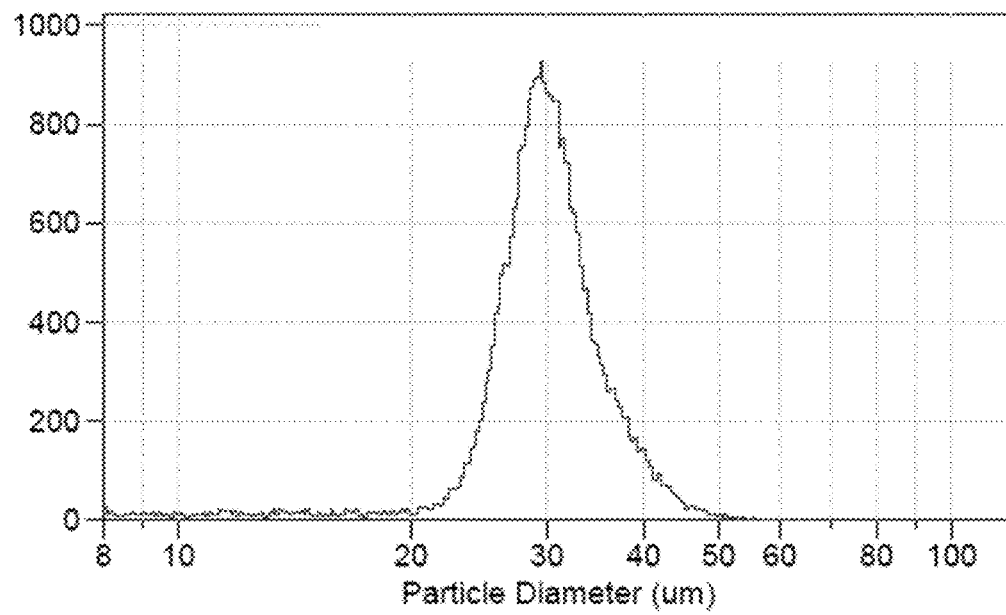
FIG. 4 shows the sizes and distributions of the microparticles according to Example 1 and Comparative Example 1 of the present invention.
Figure 4:
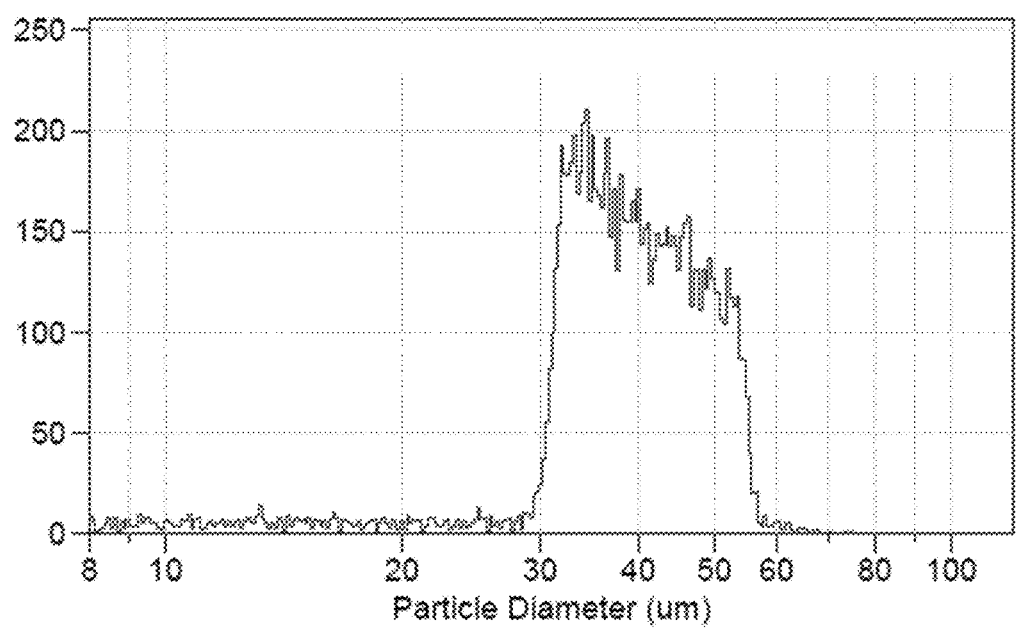

The particle sizes and distributions of porous microparticles of biodegradable polymer prepared in the above Example 1 and the microparticles of Comparative Example 1 were measured. The results are shown in FIG. 4. As shown in FIG. 4, it can be confirmed that as compared with the microparticles of Comparative Example 1, the porous microparticles of biodegradable polymer according to the present invention were generally smaller (Example 1: 20 to 40 μm, Comparative Example 1: 30 to 50 μm) and more uniform in light of the average value, and showed narrower distribution. The results are shown in Table 1.

TABLE 1

|  | $D_{10}$ | $D_{50}$ | $D_{90}$ | C.V.[1)] | span |
|---|---|---|---|---|---|
| Example 1 | 24.92 μm | 29.82 μm | 36.59 μm | 19.1% | 0.391 |
| Comparative Example 1 | 31.06 μm | 38.83 μm | 51.01 μm | 24.3% | 0.514 |

[1)]C.V. (coefficient of variation): The value of dividing standard deviation by average, and the standard for measuring the degree of relative dispersion. As the calculated value is closer to 0, it means that the particles are populated on the average and the degree of dispersion is small.

Experimental Example 3

Figure 5:
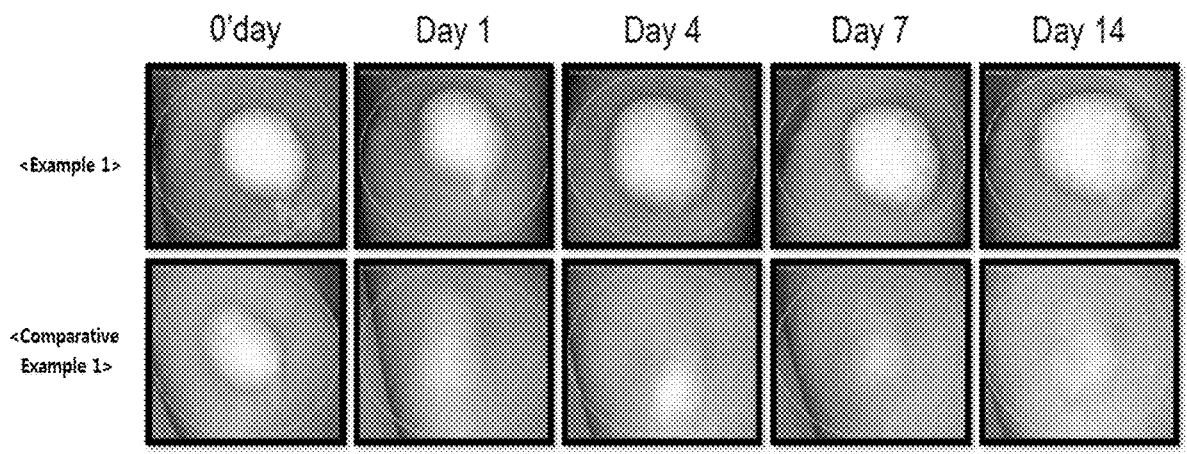
FIG. 5 shows photographs of injection parts taken after the injection of the polymer filler prepared in Example 1 and the filler of Comparative Example 1 of the present invention into mice.

The mixed formulation was filled within a syringe and 200 μl thereof was injected into the back of a hairless mouse. The polymer fillers prepared in Examples 1 to 7 and the polymer fillers of Comparative Examples 1 and 2 were injected into the mice, and the photographs of the injection parts were taken for 2 weeks and are shown in FIG. 5. The sizes of the injection parts were measured, and the size changes were periodically checked continuously. The results are shown in Table 2.

As shown in Table 2, as for the filler formulation comprising the porous microparticles of biodegradable polymer according to the present invention, it can be confirmed that the initial volume reduction after the procedure was improved remarkably.

TABLE 2

|  | Example 1 | Example 2 | Example 3 | Example 4 | Example 5 | Example 6 | Example 7 | Comp. Example 1 | Comp. Example 2 |
|---|---|---|---|---|---|---|---|---|---|
| Volume immediately after the procedure | 100% | 100% | 100% | 100% | 100% | 100% | 100% | 100% | 100% |

TABLE 2-continued

|  | Example 1 | Example 2 | Example 3 | Example 4 | Example 5 | Example 6 | Example 7 | Comp. Example 1 | Comp. Example 2 |
|---|---|---|---|---|---|---|---|---|---|
| Volume after 1 week | 90% | 95% | 95% | 100% | 90% | 95% | 85% | 50% | 10% |
| Volume after 3 months | 100% | 105% | 100% | 110% | 100% | 100% | 95% | 80% | 60% |

The invention claimed is:

1. Porous microparticle of biodegradable polymer, having
i) spherical shape,
ii) particle diameter of 10 to 50 μm,
iii) pore with a diameter of 0.1 to 10 μm, and
iv) porosity ratio of 10 to 20%; and
$d_{10}$ of greater than 20 μm, $d_{90}$ of less than 60 μm, and a span value of less than 0.8;
wherein the span value is calculated by the following equation:

$$\text{span} = \frac{D_{90} - D_{10}}{D_{50}}$$

wherein $D_{10}$, $D_{50}$ and $D_{90}$ represent size values corresponding to 10%, 50%, and 90%, respectively, of the maximum value in accumulated distribution of particles, represented as the particle sizes corresponding to 1/10, 5/10, and 9/10, respectively, of the particle size distribution curve showing the relatively accumulated amounts of particles according to the size when it is measured, plotted and divided into 10 fractions;
wherein the biodegradable polymer is at least one selected from the group consisting of poly(lactic acid), poly(glycolic acid), poly(dioxanone), poly(caprolactone), poly(lactic acid-co-glycolic acid), poly(dioxanone-co-caprolactone), poly(lactic acid-co-caprolactone), derivatives thereof and copolymers thereof.

2. The porous microparticle of biodegradable polymer according to claim 1, wherein the biodegradable polymer has a number average molecular weight (Mn) in a range of 10,000 to 1,000,000 g/mol.

3. Polymer filler comprising:
the porous microparticle of biodegradable polymer according to claim 1; and
one or more biocompatible carriers.

4. The polymer filler according to claim 3, wherein the biocompatible carrier is selected from carboxymethyl cellulose, hyaluronic acid, dextran, collagen and combinations thereof.

5. The polymer filler according to claim 3, wherein, based on 100% by weight of the polymer filler, the amount of the porous microparticle of biodegradable polymer is 10 to 50% by weight and the amount of the biocompatible carrier is 50 to 90% by weight.

6. The polymer filler according to claim 3, which is prepared in an injection formulation.

7. The polymer filler according to claim 3, which is used for wrinkle improvement, facial plastic procedure or body plastic procedure.

* * * * *